US010562225B2

(12) United States Patent
Johnson

(10) Patent No.: US 10,562,225 B2
(45) Date of Patent: Feb. 18, 2020

(54) SYSTEM FOR MANUFACTURING FIBER SCAFFOLDS FOR USE IN TRACHEAL PROSTHESES

(71) Applicant: NANOFIBER SOLUTIONS, INC., Hilliard, OH (US)

(72) Inventor: Jed K. Johnson, London, OH (US)

(73) Assignee: NANOFIBER SOLUTIONS, LLC, Hilliard, OH (US)

( * ) Notice: Subject to any disclaimer, the term of this patent is extended or adjusted under 35 U.S.C. 154(b) by 300 days.

(21) Appl. No.: 14/570,853

(22) Filed: Dec. 15, 2014

(65) Prior Publication Data

US 2015/0132423 A1    May 14, 2015

Related U.S. Application Data

(62) Division of application No. 13/677,644, filed on Nov. 15, 2012, now Pat. No. 10,239,262.

(Continued)

(51) Int. Cl.
*B29C 67/00*    (2017.01)
*A61F 2/20*    (2006.01)
(Continued)

(52) U.S. Cl.
CPC ............ *B29C 64/00* (2017.08); *A61F 2/04* (2013.01); *A61F 2/20* (2013.01); *A61L 27/3612* (2013.01);
(Continued)

(58) Field of Classification Search
CPC ........ A61F 2/20; A61F 2240/005; A61F 2/04; A61F 2002/046; A61F 2002/043;
(Continued)

(56) References Cited

U.S. PATENT DOCUMENTS 4,738,740 A    4/1988  Pinchuk et al.
5,258,027 A    11/1993 Berghaus
(Continued)

FOREIGN PATENT DOCUMENTS

AU    2009207489 B2    9/2014
CN    102008755 A    4/2011
(Continued)

OTHER PUBLICATIONS

Breatnach et al., "Dimensions of the Normal Human Trachea," Journal of Roentgenology (May 1984), 142(5) pp. 903-906.
(Continued)

*Primary Examiner* — Seyed Masoud Malekzadeh
(74) *Attorney, Agent, or Firm* — Pepper Hamilton LLP

(57) ABSTRACT

A system for manufacturing a synthetic organ suitable for transplantation into a biological organism is provided. This synthetic organ includes a three-dimensional polymer scaffold, wherein the shape and dimensions of the polymer scaffold are based on a native organ, wherein the polymer scaffold further includes at least one layer of polymer fibers that have been deposited by electrospinning, and wherein the orientation of the fibers in the scaffold relative to one another is generally parallel, random, or both; and wherein the polymer scaffold has been preseeded with at least one type of biological cell prior to implantation into a biological organism, and wherein the at least one type of biological cell is operative to facilitate integration of the polymer scaffold into the organism so that the polymer scaffold may function in a manner significantly similar to or the same as the native organ.

11 Claims, 5 Drawing Sheets

Related U.S. Application Data

(60) Provisional application No. 61/562,090, filed on Nov. 21, 2011, provisional application No. 61/596,960, filed on Feb. 9, 2012, provisional application No. 61/660,048, filed on Jun. 15, 2012.

(51) Int. Cl.

| | | |
|---|---|---|
| *B29C 64/00* | (2017.01) | |
| *A61L 27/36* | (2006.01) | |
| *A61L 27/38* | (2006.01) | |
| *A61L 27/40* | (2006.01) | |
| *A61F 2/04* | (2013.01) | |
| *B29K 67/00* | (2006.01) | |
| *B29K 75/00* | (2006.01) | |
| *B29K 311/00* | (2006.01) | |

(52) U.S. Cl.
CPC ........... *A61L 27/3882* (2013.01); *A61L 27/40* (2013.01); *A61F 2002/043* (2013.01); *A61F 2002/046* (2013.01); *A61F 2240/005* (2013.01); *A61L 2430/22* (2013.01); *B29K 2067/003* (2013.01); *B29K 2075/00* (2013.01); *B29K 2311/00* (2013.01)

(58) Field of Classification Search
CPC . B29C 67/0051; B29C 64/00; B29K 2311/00; B29K 2075/00; B29K 2067/003; A61L 27/3612; A61L 27/3882; A61L 27/40; A61L 27/18; A61L 29/06; A61L 2430/22; C08L 77/12
See application file for complete search history.

(56) References Cited

U.S. PATENT DOCUMENTS

| | | | | |
|---|---|---|---|---|
| 5,628,788 | A * | 5/1997 | Pinchuk | A61F 2/07 606/194 |
| 6,143,022 | A | 11/2000 | Shull et al. | |
| 7,115,220 | B2 | 10/2006 | Dubson et al. | |
| 7,172,765 | B2 | 2/2007 | Chu et al. | |
| 7,220,281 | B2 | 5/2007 | Lambrecht et al. | |
| 7,390,760 | B1 | 6/2008 | Chen et al. | |
| 7,490,563 | B2 * | 2/2009 | Eastin | A01C 1/04 111/118 |
| 7,629,030 | B2 | 12/2009 | Robertson et al. | |
| 7,718,351 | B2 | 5/2010 | Ying et al. | |
| 7,993,567 | B2 | 8/2011 | Scott-Carrell et al. | |
| 8,157,722 | B2 | 4/2012 | Arnal et al. | |
| 2002/0090725 | A1 | 7/2002 | Simpson et al. | |
| 2002/0142458 | A1 | 10/2002 | Williams et al. | |
| 2003/0168756 | A1 | 9/2003 | Balkus, Jr. et al. | |
| 2003/0211130 | A1 | 11/2003 | Sanders et al. | |
| 2003/0226750 | A1 * | 12/2003 | Fenn | B05B 5/002 204/164 |
| 2005/0177249 | A1 | 8/2005 | Kladakis et al. | |
| 2005/0220848 | A1 * | 10/2005 | Bates | A61F 2/06 424/443 |
| 2005/0277985 | A1 | 12/2005 | Wert et al. | |
| 2006/0060999 | A1 * | 3/2006 | Amagasa | D01D 5/0069 264/10 |
| 2006/0085063 | A1 | 4/2006 | Shastri et al. | |
| 2006/0134157 | A1 | 6/2006 | Lehman et al. | |
| 2006/0135020 | A1 | 6/2006 | Weinberg et al. | |
| 2006/0154063 | A1 * | 7/2006 | Fujihara | A61L 27/18 428/373 |
| 2006/0204539 | A1 | 9/2006 | Atala et al. | |
| 2007/0142907 | A1 | 6/2007 | Moaddeb et al. | |
| 2007/0191956 | A1 | 8/2007 | Prewett et al. | |
| 2007/0232169 | A1 * | 10/2007 | Strickler | A61L 15/225 442/181 |
| 2007/0269481 | A1 * | 11/2007 | Li | A61L 27/18 424/423 |
| 2007/0286880 | A1 | 12/2007 | Vasiliev et al. | |
| 2008/0208323 | A1 | 8/2008 | El-Kurdi et al. | |
| 2008/0208358 | A1 | 8/2008 | Bellamkonda et al. | |
| 2009/0018643 | A1 * | 1/2009 | Hashi | A61F 2/82 623/1.15 |
| 2009/0108503 | A1 * | 4/2009 | Scott-Carnell | D01D 5/0084 264/484 |
| 2009/0143855 | A1 * | 6/2009 | Weber | A61F 2/91 623/1.42 |
| 2009/0152773 | A1 * | 6/2009 | Barinov | D01D 5/0092 264/465 |
| 2009/0162468 | A1 * | 6/2009 | Barinov | D01D 5/0092 425/145 |
| 2009/0253328 | A1 * | 10/2009 | Watanabe | D01D 5/0038 442/327 |
| 2010/0082114 | A1 | 4/2010 | Gingras et al. | |
| 2010/0105799 | A1 | 4/2010 | Rudd et al. | |
| 2010/0166854 | A1 | 7/2010 | Michniak-Kohn et al. | |
| 2010/0222771 | A1 * | 9/2010 | Mitchell | A61L 27/14 606/1 |
| 2010/0233115 | A1 * | 9/2010 | Patel | A61L 15/26 424/78.08 |
| 2010/0273258 | A1 | 10/2010 | Lannutti et al. | |
| 2010/0303881 | A1 | 12/2010 | Hoke et al. | |
| 2011/0022149 | A1 | 1/2011 | Cox et al. | |
| 2011/0028834 | A1 | 2/2011 | Zussman | |
| 2011/0030885 | A1 | 2/2011 | Anneaux et al. | |
| 2011/0070283 | A1 | 3/2011 | Hossainy et al. | |
| 2011/0083987 | A1 | 4/2011 | Rolland et al. | |
| 2011/0098826 | A1 | 4/2011 | Mauck et al. | |
| 2011/0166647 | A1 | 7/2011 | Hashi et al. | |
| 2011/0177395 | A1 | 7/2011 | Kamisasa | |
| 2011/0270412 | A1 | 11/2011 | Bellan et al. | |
| 2012/0068384 | A1 | 3/2012 | Phaneuf et al. | |
| 2012/0093717 | A1 | 4/2012 | Mauck et al. | |
| 2012/0271405 | A1 | 10/2012 | Soletti | |
| 2013/0103079 | A1 | 4/2013 | Lau et al. | |
| 2013/0150963 | A1 | 6/2013 | Johnson | |
| 2013/0310920 | A1 | 11/2013 | Su | |
| 2014/0030315 | A1 | 1/2014 | Johnson | |
| 2014/0057346 | A1 | 2/2014 | Johnson | |
| 2014/0072951 | A1 | 3/2014 | Johnson | |
| 2014/0272225 | A1 | 9/2014 | Johnson | |
| 2014/0309726 | A1 | 10/2014 | Wang | |
| 2017/0182206 | A1 | 6/2017 | Johnson et al. | |
| 2019/0249127 | A1 | 8/2019 | Johnson | |

FOREIGN PATENT DOCUMENTS

| | | |
|---|---|---|
| EP | 0416846 A2 | 3/1991 |
| EP | 242203 | 10/2010 |
| JP | 2012-527217 A | 11/2012 |
| WO | WO 2000/010622 A1 | 3/2000 |
| WO | WO 2001/015754 A1 | 3/2001 |
| WO | WO 2005/012606 A2 | 2/2005 |
| WO | WO 2005/096989 A1 | 10/2005 |
| WO | WO 2006/138552 A2 | 12/2006 |
| WO | WO 2008/137659 A1 | 11/2008 |
| WO | WO 2009/089035 A1 | 7/2009 |
| WO | WO 2010/040129 A3 | 4/2010 |
| WO | WO 2010/048281 A1 | 4/2010 |
| WO | WO 2010/124207 A1 | 10/2010 |
| WO | WO 2013/078051 A1 | 5/2013 |
| WO | WO 2013/106822 A1 | 7/2013 |
| WO | WO 2014/031721 A1 | 2/2014 |
| WO | WO 2014/145864 A1 | 9/2014 |
| WO | WO 2015/153011 A1 | 10/2015 |

OTHER PUBLICATIONS

Erbel et al., "Aortic Dimensions and the Risk of Dissection," Heart (Jan. 2006), 92(1) pp. 137-142.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.

(56) References Cited

OTHER PUBLICATIONS

Samios et al., "In situ compatibilization of polyurethane with poly(ethylene terephthalate)," Department of Chemistry, European Polymer Journal (2000), 36 pp. 937-947.
Frey et al. "Electrospinning and Porosity Measurements of Nylon6 PEO blended Nonwovens" Journal of Engineered Fibers and Fabrics (2007), 2(1):31-37.
Hashi et al. "Antithrombogenic Modification of Small Diameter Microfibrous Vascular Grafts" Arterioscler Thromb Vasc Biol. (Aug. 2010), 30(8):1621-1627.
Meng et al., Journal of Nanoscience and Nanotechnology (Jul. 8, 2010), 312-320.
International Search Report and Written Opinion for PCT/US2016/030058 dated Jul. 29, 2016.
Aboitiz et al. "Fiber composition of the human corpus callosum" (Dec. 11, 1992) *Brain Res.* 598(1-2):143-153 (Abstract only).
Albertini et al. "The effect of glycosaminoglycans and proteoglycans on lipid peroxidation" (Aug. 2000) *Int. J. Mol. Med.* 6(2):129-136 (Abstract only).
Alexis et al. "In Vivo Particle Uptake by Airway Macrophages in Healthy Volunteers" (2006) *Am. J. Respir. Cell Mol. Biol.* 34(3):305-313.
Band et al. "Antiproliferative effect of gossypol and its optical isomers on human reproductive cancer cell lines" (Mar. 1989) *Gynecologic Oncology* 32(3):273-277 (Abstract only).
Bandtlow et al. "Proteoglycans in the developing brain: new conceptual insights for old proteins" (Oct. 2000) *Physiol. Rev.* 80(4):1267-1290.
Baran et al. "Important roles for macrophage colony-stimulating factor, CC chemokine ligand 2, and mononuclear phagocytes in the pathogenesis of pulmonary fibrosis" (2007) *Am. J. Respir. Crit. Care Med.* 176(1):78-89.
Bellail et al. "Microregional extracellular matrix heterogeneity in brain modulates glioma cell invasion" (Jun. 2004) *Int. J. Biochem. Cell Biol.* 36(6):1046-1069 (Abstract only).
Beningo et al. "Nascent Focal Adhesions Are Responsible for the Generation of Strong Propulsive Forces in Migrating Fibroblasts" (May 14, 2001) *J. Cell Biol.* 153(4):881-887.
Benz et al. "Biochemical Correlates of the Antitumor and Antimitochondrial Properties of Gossypol Enantiomers" (Jun. 1990) *Mol. Pharma.* 37(6):840-847 (Abstract only).
Benz et al. "Lactic Dehydrogenase Isozymes, $^{31}$P Magnetic-Resonance Spectroscopy, and In Vitro Antimitochondrial Tumor Toxicity With Gossypol and Rhodamine-123" (Feb. 1987) *J. Clin. Invest.* 79(2):517-523.
Benz et al. "Selective toxicity of gossypol against epithelial tumors and its detection by magnetic resonance spectroscopy" (Mar. 1988) *Contraception* 37(3):221-228 (Abstract only).
Bernstein et al. "Glioblastoma cells do not intravasate into blood vessels" (Jan. 1995) *Neurosurgery* 36(1):124-132 (Abstract only).
Bershadsky et al. "Adhesion-mediated mechanosensitivity: a time to experiment, and a time to theorize" (Oct. 2006) *Curr. Opn. Cell Biol.* 18(5):472-481 (Abstract only).
Binder et al. "Proteases and the Biology of Glioma Invasion" (2002) *J. Neuro-Oncology* 56:149-158.
Bucala et al. "Circulating Fibrocytes Define a New Leukocyte Subpopulation That Mediates Tissue Repair" (Nov. 1994) *Mol. Med.* 1(1):71-81 (Abstract only).
Camoretti-Mercado "Targeting the airway smooth muscle for asthma treatment" (Oct. 2009) *Translational Research* 154(4):165-174 (Abstract only).
Cattaruzza et al. "Proteoglycan control of cell movement during wound healing and cancer spreading" (Sep. 2005) *Matrix Biol.* 24(6):400-417 (Abstract only).
Central Brain Tumor Registry of the United States, Primary Brain Tumors in the United States—Statistical Report 1998-2002, *CBTRUS* 2005-2006.
Chalmers et al. "Chapter 9. Preparative applications of magnetic separation in biology and medicine" (2007) *Laboratory Techniques in Biochemistry and Molecular Biology* 32:249-264 (Abstract only).

Chen et al., Preparation and Characterization of Coaxial Electrospun Thermoplastic Polyurethane/Collagen Compound Nanofibers for Tissue Engineering Applications, *Colloids and Surfaces B-Biointerfaces* (2010), 79(2):315-325.
Chew et al. "The Role of Electrospinning in the Emerging Field of Nanomedicine" 2006, *Curr. Pharm. Sec.* 12(36)A:4751-4770.
Chicoine et al. "Assessment of brain-tumor cell motility in vivo and in vitro" (Apr. 1995) *J. Neurosurg.* 82(4):615-622 (Abstract only).
Choi et al. "Structuring electrospun polycaprolactone nanofiber tissue scaffolds by femtosecond laser ablation" (Nov. 2007) *J. Laser Appl.* 19(4):225-231.
Cukierman et al. "Taking cell-matrix adhesions to the third dimension" (Nov. 23, 2001) *Science* 294:1708-1712.
Dahl et al., "Readily Available Tissue-Engineered Vascular Grafts" (2011) *Science Translational Medicine*, 3(68).
Davies et al. "Adult axon regeneration in adult CNS white matter" (Dec. 1, 1998) *Trends Neurosci.* 21(12):515.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) *Adv. Funct. Mater.* 16(16):2110-2116.
Discher et al. "Tissue cells feel and respond to the stiffness of their substrate" (Nov. 18, 2005) *Science* 310:1139-1143.
Drilling et al. "Fabrication of burst pressure competent vascular grafts via electrospinning: Effects of microstructure" (Mar. 15, 2009) *J. Miomed. Mat. Res. Part A* 88A(4):923-934 (Abstract only).
Duling et al. "Mechanical characterization of electrospun Polycaprolactone (PCL): a potential scaffold for tissue engineering" (Feb. 2008) *J. Biomech. Eng.* 130(1) No. 011006 (Abstract only).
Engler et al. "Matrix Elasticity Directs Stem Cell Lineage Specification" (Aug. 25, 2006) *Cell* 126(4):677-689.
Epperly et al. "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules" (2004) *In Vivo* 18(1):1-14.
Farin et al. "Transplanted glioma cells migrate and proliferate on host brain vasculature: a dynamic analysis" (Jun. 2006) *Glia* 53(8):799-808 (Abstract only).
Fathallah-Shaykh "Darts in the Dark Cure Animal, but Not Human, Brain Tumors" (May 2002) *Arch. Neurol.* 59:721-724 (Abstract only).
Fujihara et al "Guided bone regeneration membrane made of Polycaprolactone/calcium carbonate composite nano-fibers" (Jul. 2005) *Biomaterials* 26(19):4139-4147 (Abstract only).
Furnari et al. "Malignant astrocytic glioma: genetics, biology, and paths to treatment" (2007) *Genes Dev.* 21:2683-2710.
Gaumer et al. "Structure-function relationships and Source-to-ground Distance and the Mechanical Properties of Electrospun Fiber" *Acta Biomaterialia* 5(5):1552-1561 (Abstract only).
Geiser et al. "The Role of Macrophages in the Clearance of Inhaled Ultrafine Titanium Dioxide Particles" (2008) *Am. J. Respir. Cell Mol. Biol.* 38(3):371-376.
Georges et al. "Cell type-specific response to growth on soft materials" (Apr. 2005) *J. Appl. Physiol.* 98:1547-1553.
Georges et al. "Matrices with compliance comparable to that of brain tissue select neuronal over glial growth in mixed coritical cultures" (Apr. 2006) *Biophys. J.* 90:3012-3018.
Giese et al. "Dichotomy of astrocytoma migration and proliferation" (1996) *Int. J. Cancer* 67:275-282.
Giese et al. "Glioma cell adhesion and migration on human brain sections" (1998) *Anticancer Res.* 18(4A):2435-2447 (Abstract only).
Giese et al. "Migration of Human Glioma Cells on Myelin" (Apr. 1996) *Neurosurgery* 38(4):755-764 (Abstract only).
Giese et al. "Substrates for astrocytoma invasion" (Aug. 1995) *Neurosurgery* 37(2):294-302 (Abstract only).
Gilbert et al. "Antiproliferative activity of gossypol and gossypolone on human breast cancer cells" (May 26, 1995) *Life Sciences* 57(1):61-67 (Abstract only).

(56) References Cited

OTHER PUBLICATIONS

Gladson "The Extracellular Matrix of Gliomas: Modulation of Cell Function" (Oct. 1999) *J. Neuropath. Exper. Neur.* 58(10):1029-1040 (Abstract only).
Goldbrunner et al. "Cell-extracellular matrix interaction in glioma invasion" (1999) *Acta Neurochir (Wien)* 141:295-305.
Grandpre et al. "Nogo: a molecular determinant of axonal growth and regeneration" (Oct. 2001) *Neuroscientist* 7(5):377-386 (Abstract only).
Haley et al. "Study of myelin purity in relation to axonal contamination" (1980) *Cell Mol. Neurobiol.* 1:175-187.
Hashi et al. "Antithrombogenic Property of Bone Marrow Mesenchymal Stem Cells in Nanofibrous Vascular Grafts" Jul. 17, 2007, *PNAS* 104(29) pp. 11915-11920.
He et al. "Fabrication of Drug-Loaded Electrospun Aligned Fibrous Threads for Suture Applications" 2009, J. Biomed. Mater. Research, Part A 89(1):80-95.
Hinz et al. "Alpha-smooth muscle actin expression upregulates fibroblast contractile activity" (Sep. 2001) *Molecular Biology of the Cell* 12(9):2730-2741.
Holland "Glioblastoma multiforme; the terminator" (Jun. 6, 2000) *PNAS USA* 97(12):6242-6244.
Hsu et al. "N,N-Dimethylformamide Additions to the Solution for the Electrospinning of Poly($\epsilon$-caprolactone) Nanofibers" (Apr. 2004) *Macromolecular Materials and Engineering* 289(4):334-340.
Hsu et al. "Nano-sized beads and porous fiber constructs of Poly($\epsilon$-caprolactone) produced by electrospinning" (2004) *Journal of Material Science* 39(9):3003-3013.
Hu et al. "Gossypol inhibits basal and estrogen-stimulated DNA synthesis in human breast carcinoma cells" (1993) *Life Sciences* 53(25):PL433-PL438 (Abstract only).
Hu et al. "Regulating axon growth within the postnatal central nervous system" (Dec. 2004) *Semin Perinatol* 28(6):371-378.
Hu et al. "The proteoglycan brevican binds to fibronectin after proteolytic cleavage and promotes glioma cell motility" (Sep. 5, 2008) *Journal of Biological Chemistry* 283(36):24848-24859.
Huang et al. "A review on polymer nanofibers by electrospinning and their applications in nanocomposites" (Nov. 2003) *Composites Science and Technology* 63(15):2223-2253 (Abstract only).
International Search Report and Written Opinion for PCT/US2015/016973 dated May 22, 2015.
Jaroszewski et al. "Action of Gossypol and Rhodamine 123 on Wild Type and Multidrug-resistant MCF-7 Human Breast Cancer Cells: $^{31}$P Nuclear Magnetic Resonance and Toxicity Studies" (1990) *Cancer Research* 50(21):6936-6943.
Johnson "First-in-the-World Equine Joint Injection for Osteoarthritis" (Jul./Aug. 2014) *The International Equine Veterinarian* 23-25.
Johnson et al. "Electrospun PCL in Vitro: a Microstructural Basis for Mechanical Property Changes" (2009) *Journal of Biomaterials Science, Polymer Edition* 20(4):467-481 (Abstract only).
Johnson et al. "Microstructure-Property Relationships in a Tissue-Engineering Scaffold" (2007) *Journal of Applied Polymer Science* 104(5):2919-2927.
Johnson et al. "Quantitative Analysis of Complex Glioma Cell Migration on Electrospun Polycaprolcatone Using Time-Lapse Microscopy" (2009) *Tissue Engineering Part C* 15(4):531-540.
Jung et al. "Tracking the invasiveness of human astrocytoma cells by using green fluorescent protein in an organotypical brain slice model" (Jan. 2001) *J. Neurosurgery* 94(1):80-89 (Abstract only).
Kang et al. Plasma Treatment of Textiles—synthetic Polymer-Base Textiles (2004) AATCC Review 4(11):29-33.
Katta et al. "Continuous electrospinning of aligned polymer nanofibers onto a wire drum collector" (Sep. 28, 2004) *Nano Letters* 4(11):2215-2218 (Abstract only).
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, *J. Gastronenter. Hepatol.* 24(2):278-287.

Khil et al. "Novel fabricated matrix via electrospinning for tissue engineering" (2005) *Journal of Biomedical Materials Research Part B—Applied Biomaterials* 72B(1):117-124.
Kim et al. "Controlled protein release from electrospun biodegradable fiber mesh composed of poly($\epsilon$-caprolactone) and poly(ethylene oxide)" (Jun. 29, 2007) *International Journal of Pharmaceutics* 338 (1-2):276-283 (Abstract only).
Kim et al. "Epithelial cell $\alpha 3\beta 1$ integrin links $\beta$-catenin and Smad signaling to promote myofibroblast formation and pulmonary fibrosis" (Jan. 2009) *Journal of Clinical Investigation* 119(1):213-224.
Kleihues et al. "The WHO Classification of Tumors of the Nervous System" (Mar. 2002) *J. Neuropathol. Exp. Neurol.* 61(3):215-225 (Abstract only).
Klim et al. "A Defined Glycosaminoglycan-Binding Substratum for Human Pluripotent Stem Cells" (2010) *Nature Methods* 7(23):989-996 (Abstract only).
Ko et al. "High Percentage of False-Positive Results of Cytokeratin 19 RT-PCR in Blood: A Model for the Analysis of Illegitimate Gene Expression" (2000) *Oncology* 59:81-88 (Abstract only).
Kwon et al. "Electrospun nano-to microfiber fabrics made of biodegradable copolyesters: structural characteristics, mechanical properties and cell adhesion potential" (Jun. 2005) *Biomaterials* 26(18):3929-3939.
Lannutti et al. "Electrospinning for tissue engineering scaffolds" (Apr. 2007) *Materials Science and Engineering: C* 27(3):504-509.
Leblanc et al. "An in vitro study of inhibitory activity of gossypol, a cottonseed extract, in human carcinoma cell lines" (Dec. 2002) *Pharmacological Research* 46(6):551-555.
Lee et al. "Characterization of nano-structured poly($\epsilon$-caprolactone) nonwoven mats via electrospinning" (Feb. 2003) *Polymer* 44(4):1287-1294.
Lesma et al. "Glycosaminoglycans in nerve injury: I. Low doses glycosaminoglycans promote neurite formation" (Dec. 1, 1996) J. Neurosci. Res. 46(5):565-571.
Levicar et al. "Proteases in brain tumour progression" (2003) *Acta Neurochir. (Wien.)* 145:825-838.
Levina et al. "Chemotherapeutic drugs and human tumor cells cytokine network" (2008) *International Journal of Cancer* 123(9):2031-2040.
Li et al. "A three-dimensional nanofibrous scaffold for cartilage tissue engineering using human mesenchymal stem cells" (Feb. 2005) *Biomaterials* 26(6):599-609.
Li et al. "Biological response of chondrocytes cultured in three-dimensional nanofibrous poly($\epsilon$-caprolactone) scaffolds" (Dec. 15, 2003) *Journal of Biomedical Materials Research Part A* 67A(4):1105-1114.
Li et al. "Electrospinning nanofibers as uniaxially aligned arrays and layer-by-layer stacked films" (Feb. 2004) *Advanced Materials* 16(4):361-366.
Li et al. "Multilineage differentiation of human mesenchymal stem cells in a three-dimensional nanofibrous scaffold" (Sep. 2005) *Biomaterials* 26(25):5158-5166.
Liang et al. "Developing gossypol derivatives with enhanced antitumor activity" (1995) *Investigational New Drugs* 13(3):181-186.
Lieblein et al. "STAT3 can be activated through paracrine signaling in breast epithelial cells" (2008) *BMC Cancer* 8(302):1-14 :302.
Liu et al. "Function analysis of estrogenically regulated protein tyrosine phosphatase $\gamma$ (PTP$\gamma$) in human breast cancer cell line MCF-7" (2004) *Oncogene* 23(6):1256-1262.
Liu et al. "Involvement of breast epithelial-stromal interactions in the regulation of protein tyrosine phosphatase-$\gamma$ (PTP$\gamma$) mRNA expression by estrogenically active agents" (2002) *Breast Cancer Research and Treatment* 71(1):21-35.
Liu et al. The (−)-enantiomer of gossypol possesses higher anticancer potency than racemic gossypol in human breast cancer: (2002) *Anticancer Research* 22(1A):33-38.
Liu et al. "Transformation of MCF-10A Human Breast Epithelial Cells by Zeranol and Estradiol-17beta" (Nov.-Dec. 2004) *Breast J.* 10(6):514-521 (Abstract only).
Lo et al. "Cell movement is guided by the rigidity of the substrate" (Jul. 2000) *Biophysical Journal* 79(1);144-152.

(56) References Cited

OTHER PUBLICATIONS

Luu et al. "Development of a nanostructured DNA delivery scaffold via electrospinning of PLGA and PLGA and PLA-PEG block copolymers" (Apr. 29, 2003) *Journal of Controlled Release* 89(2):341-353.
Macchiarini et al. "Clinical Transplantation of a Tissue-Engineered Airway" (Dec. 13, 2008) *The Lancet* 372(9655):2023-2030.
Martins et al. "Electrospun nanostructured scaffolds for tissue engineering applications" (2007) *Nanomedical* 2(6):929-942.
Mathews, "Preparation and anisotropic mechanical behavior of highly-oriented electrospun poly(butylene terephthalate) fibers" (Aug. 2006) *Journal of Applied Polymer Science* 101(3):2017-2021.
McClure et al. "A Three-Layered Electrospun Matrix to Mimic Native Arterial Architecture Using Polycaprolactone, Elastin, and Collagen: A Preliminary Study" 2010, *Acta Biomaterialia* 6:2422-2433.
Morawski et al. "Paineuronal nets potentially protect against oxidative stress" (Aug. 2004) *Exp. Neurol.* 188(2):309-315.
Morgenstern et al. "Chondroitin sulphate proteoglycans in the CNS injury response" (2002) *Prog. Brain Res.* 137:313-332.
Mori et al. "Fibrocytes contribute to the myofibroblast population in wounded skin and originate from the bone marrow" (Mar. 10, 2005) *Experimental Cell Research* 304(1):81-90.
Murray et al. "Hyper-responsiveness of IPF/UIP fibroblasts: Interplay between TGF β1, IL-13 and CCL2" (2008) 40(10):2174-2182.
Nam et al. "Improved Cellular Infiltration in Electrospun Fiber via Engineered Porosity" (Sep. 2007) *Tissue Engineering* 13(9):2249-2257.
Nam et al. "Materials selection and residual solvent retention in biodegradable electrospun fibers" (Feb. 5, 2008) *Journal of Applied Polymer Science* 107(3):1547-1524.
Nam et al. "Modulation of Embryonic Mesenchymal Progenitor Cell Differentiation via Control Over Pure Mechanical Modulus in Electrospun Nanofibers" (Apr. 2011) *Acta Biomaterialia* 7(4): 1516-1524.
Nam et al. "Novel Electrospun Scaffolds for the Molecular Analysis of Chondrocytes Under Dynamic Compression" 2009, *Tissue Engineering Part A* 15(3):513-523.
Ninomiya et al. "Transforming Growth Factor—β Signaling Enhances Transdifferentiation of Macrophages into Smooth Muscle-Like Cells" (2006) *Hypertension Research* 29(4):269-276.
Norton et al. "Myelination in rat brain: method of myelin isolation" (Oct. 1973) *J Neurochem.* 21(4):749-757.
Novak et al. "Extracellular matrix and the brain: components and function" (2000) *J. Clin. Neurosci.* 7(4):280-290.
Ohnishi et al. "A Novel Model of Glioma Cell Invasion Using Organotypic Brain Slice Culture" (Jul. 15, 1998) *Cancer Res.* 58:2935-2940.
Palfi et al. "Correlation of in vitro infiltration with glioma histological type in organotypic brain slices" (2004) *Br. J. Cancer* 91(4):745-752.
Pelham Jr. et al. "Cell locomotion and focal adhesions are regulated by substrate flexibility" (Dec. 1997) *PNAS USA* 94:13661-13665.
Pham et al., Electrospinning of Polymeric Nanofibers for Tissue Engineering Applications: A Review, Tissue Engineering (2006), 12(5):1197-1211.
Pilkington "The paradox of neoplastic glial cell invasion of the brain and apparent metastatic failure" (1997) *Anticancer Res.* 17(6B):4103-4105 (Abstract).
Powell et al. "EDC cross-linking improves skin substitute strength and stability" (2006) *Biomaterials* 27(34): 5821-5827.
Properzi et al. "Proteoglycans and Brain Repair" (Feb. 2004) *News Physiol. Sci.* 19:33-38.
Quigley et al. "The relationship between survival and the extent of the resection in patients with supratentorial malignant gliomas" (1991) *Neurosurgery* 29:385-389.
Rao "Molecular mechanisms of glioma invasiveness: the role of proteases" (Jul. 2003) *Nature Reviews Cancer* 3:489-501.
Rath et al. "Compressive Forces Induce Osteogenic Gene Expression in Calvarial Osteoblasts" (2008) *Journal of Biomechanics* 41(5):1095-1103.
Rauch "Extracellular matrix components associated with remodeling processes in brain" (2004) *Cell Mol. Life Sci.* 61:203102045.
Reneker et al. "Nanometre diameter fibres of polymer, produced by electrospinning" (1996) *Nanotechnology* 7(3):216-223.
Rocks et al. "ADAMTS-1 Metalloproteinase Promotes Tumor Development through the Induction of a Stromal Reaction In vivo" (2008) *Cancer Research* 68(22):9541-9550.
Ruoslahti "Brain extracellular matrix" (1996) Glycobiologhy 6(5):489-492.
Sasmono et al. "A macrophage colony-stimulating factor—green fluorescent protein transgene is expressed throughout the mononuclear phagocyte system of the mouse" (2003) *Blood* 101(3):1155-1163.
Saunders et al. "Fibrocyte localization to the airway smooth muscle is a feature of asthma" (Feb. 2009) *Journal of Allergy and Clinical Immunology* 123(2): 376-384.
Schiffer et al. "Cell proliferation and invasion in malignant gliomas" (1997) *Anticancer Research* 17(1A):61-69 (Abstract only).
Schmidt et al. "Identification of Circulating Fibrocytes as Precursors of Bronchial Myofibroblasts in Asthma" (2003) *Journal of Immunology* 171(1):380-389.
Shin et al. "Contractile cardiac grafts using a novel nanofibrous mesh" (Aug. 2004) *Biomaterials* 25(17):3717-3723.
Shin et al. "In Vivo Bone Tissue Engineering Using Mesenchymal Stem Cells on a Novel Electrospun Nanofibrous Scaffold" (Jul. 9, 2004) *Tissue Engineering* 10(1-2):33-41.
Sieben et al. "PCR artifacts in LOH and MSI analysis of microdissected tumor cells" (Nov. 2000) *Human Pathology* 31(11):1414-1419.
Silver et al. "Regeneration beyond the glial scar" (Feb. 2004) *Nature* 5:146-156.
Srikar et al. "Desorption-limited mechanism of release from polymer nanofibers" (2008) *Langmuir* 24(3):965-974.
Stein et al. "Estimating the cell density and invasive radius of three-dimensional glioblastoma tumor spheroids grown in vitro" (Aug. 1, 2007) *Applied Optics* 46(22):5110-5118.
Stitzel et al. "Controlled Fabrication of a Biological Vascular Substitute" 2006, *Biomaterials* 27:1088-1094.
Subramanian et al. "Metastasis to and from the central nervous system—the 'relatively protected site'" (Aug. 2002) *The Lancet Oncology* 3(8):498-507.
Swanson et al. "A quantitative model for differential motility of gliomas in grey and white matter" (Oct. 2000) *Cell Proliferation* 33(5):317-329.
Swanson "Quantifying glioma cell growth and invasion in vitro" (2008) *Mathematical and Computer Modeling* 47:638-648.
Teo et al. "A review on electrospinning design and nanofibre assemblies" (2006) *Nanotechnology* 17(14):R89-R106.
Teo et al. "Electrospun fibre bundle made of aligned nanofibers over two fixed points" (1978) *Nanotechnology* 16:1878-1884.
Thomas et al. "Effects of gossypol on the cell cycle phases in T-47D human breast cancer cells" (Jul.-Aug. 1991) *Anticancer Research* 11(4):1469-1476 (Abstract only).
Tomlinson et al. "Loss of heterozygosity analysis: Practically and conceptually flawed?" (2002) *Genes Chromosomes & Cancer* 34:349-353.
Tonn et al. "Mechanisms of glioma cell invasion" (2003) *Acta Neurochir* Suppl 88: 163-167.
Toole "Hyaluronan and its binding proteins, the hyaladherins" (1990) *Curr. Opin. Cell Biol.* 2:839-844.
Tse, et al. "Current Status of Pipeline Embolization Device in the Treatment of Intracranial Aneurysms: A review" (Dec. 2013) *World Neurosurgery* 80(6): 829-835.
Tuszynski et al. "Differential cytotoxic effect of gossypol on human melanoma, colon carcinoma, and other tissue culture cell lines" (Feb. 1984) *Cancer Research* 44(2):768-771.
Van Meter et al. "The role of matrix metalloproteinase genes in glioma invasion: co-dependent and interactive proteolysis" (2001) *Journal of Neuro-Oncology* 53:213-235.

(56) References Cited

OTHER PUBLICATIONS

Viapiano et al. "BEHAB/brevican requires ADAMTS-mediated proteolytic cleavage to promote glioma invasion" (2008) *J. Neurooncol.* 88:261-272.

Viapiano et al. "From barriers to bridges: chondroitin sulfate proteoglycans in neuropathology" (Oct. 2006) *Trends Mol. Med.* 12(10):488-496.

Vuorinen et al. "Debulking or biopsy of malignant glioma in elderly people—a 10andomized study" (2003) *Acta Neurochir.* 145:5-10.

Wang et al. "Conjugated Linoleic Acid (CLA) Up-regulates the Estrogen-regulated Cancer Suppressor Gene, Protein Tyrosine Phosphatase γ (PTPγ), in Human Breast Cells" (2006) *Anticancer Research* 26(1A):27-34.

Wang et al. "Effect of gossypol on DNA synthesis and cell cycle progression of mammalian cells in vitro" (Jan. 1984) *Cancer Research* 44(1):35-38.

Wang et al. "Nanofibres and their Influence on Cells for Tissue Regeneration" (2005) *Aust. J. Chem.* 58(10):704-712.

Wang et al. "Increased Circulating Fibrocytes in Asthma with Chronic Airflow Obstruction" (2008) *Am. J. Respir. Crit. Care Med.* 178(6): p. 583-591.

Williams et al. "Anti-glioma effects of protein kinase inhibitors that simultaneously block invasion and proliferation" (Oct. 2007) Abstracts from 12$^{th}$ Annual Meeting of the Society for Neuro-Oncology 9: 486 ET-18 (Abstract only).

Wu et al. "Versican protects cells from oxidative stress-induced apoptosis" (Feb. 2005) *Matrix Biology* 24(1):3-13.

Wu et al. "An in vitro and in vivo study of antitumor effects of gossypol on human SW-13 adrenocortical carcinoma" (1986) *Cancer Research* 49(14):3754-3758.

Wykosky et al. "Soluble monomeric EphrinA1 is released from tumor cells and is a functional ligand for the EphA2 receptor" (2008) *Oncogene* 27(58):7260-7273.

Xie et al. "Encapsulation of protein drugs in biodegradable microparticles by co-axial electrospray" Jan. 15, 2008) *Journal of Colloid and Interface Science* 317(2):469-476.

Xie et al. "White matter inhibitors in CNS axon regeneration failure" (Feb. 2007) *Exp. Neurol.* 209(2):302-312.

Yamaguchi "Lecticans: organizers of the brain extracellular matrix" (2000) *Cell Mol. Life Sci.* 57:276-289.

Yang et al. "Integrin α1β1 and α2β1 are the key regulators of hepatocarcinoma cell invasion across the fibrotic matrix microenvironment" (Dec. 1, 2003) *Cancer Research* 63(23): 8312-8317.

Yoo et al. "Surface-Functionalized Electrospun Nanofibers for Tissue Engineering and Drug Delivery" Jan. 1, 2009, *Advanced Drug Delivery Reviews* 61:1033-1042.

Yoshimoto et al. "A biodegradable nanofiber scaffold by electrospinning and its potential for bone tissue engineering" (May 2003) *Biomaterials* 24(12):2077-2082.

Yu et al. "Production of submicrometer diameter fibers by two-fluid electrospinning" (Sep. 2004) *Adv. Mater.* 16(17):1562-1566.

Zborowski et al. "Red blood cell magnetophoresis" (Apr. 2003) *Biophysical Journal* 84:2638-2645.

Zeng et al. "Enzymatic degradation of poly(L-lactide) and poly(ϵ-caprolactone) electrospun fibers" (Dec. 15, 2004) *Macromolecular Bioscience* 4(12):1118-1125.

Zeng et al. "Ultrafine fibers electrospun from biodegradable polymers" (Jul. 25, 2003) *Journal of Applied Polymer Science* 89(4): 1085-1092.

Zhang et al. "Electrospinning of gelatin fibers and gelatin/PCL composite fibrous scaffolds" (2005) *J. Biomed. Mater. Res. Part B: Appl. Biomater.* 72B(1):156-165.

Zhang et al. "Recent development of polymer nanofibers for biomedical and biotechnological applications" (2005) *Journal of Materials Science—Materials in Medicine* 16(10):933-946.

Ayres et al., "Microvascular Endothelial Cell Migration in Scaffolds of Electrospun Collagen," Wound Repair and Regeneration (Mar. 2005), 13(2):A6 (abstract only).

Park, Lab-made organ implanted for first time (Jul. 14, 2017), CNN.com, <http://www.cnn.com/2011/HEALTH/07/07/trachea.transplant/index.html>.

Barnhart et al. "Evaluation of an intra-articular synthetic ligament for treatment of cranial cruciate ligament disease in dogs: a six-month prospective clinical trial" Jun. 2016, Vet Comp Orthop. Traumatol. 29:491-498.

Supplemental European Search Report and Written Opinion for EP15774154 dated Sep. 22, 2017.

Baker et al. "The Potential to Improve Cell Infiltration in Composite Fiber-Aligned Electrospun Scaffolds by the Selective Removal of Sacrificial Fibers", Biomaterials, May 2008, pp. 2348-2358, vol. 29, Issue 15, Elsevier. DOI: 10.1016/j.biomaterials.2008.01.032.

* cited by examiner

SYSTEM FOR MANUFACTURING FIBER SCAFFOLDS FOR USE IN TRACHEAL PROSTHESES

CROSS-REFERENCE TO RELATED APPLICATIONS

This patent application is a divisional of U.S. patent application Ser. No. 13/677,644 filed on Nov. 15, 2012, now issued as U.S. Pat. No. 10,239,262, entitled "Fiber Scaffolds for Use in Tracheal Prostheses", which claimed the benefit of U.S. Provisional Patent Application Ser. No. 61/562,090 filed on Nov. 21, 2011 and entitled "Nanofiber Scaffolds for Biological Structures"; U.S. Provisional Patent Application Ser. No. 61/596,960 filed on Feb. 9, 2012 and entitled "Fiber Scaffolds for Use in Esophageal Prostheses"; and U.S. Provisional Patent Application Ser. No. 61/660,048 filed on Jun. 15, 2012 and entitled "Fiber Scaffolds for Use in Tracheal Prostheses"; the disclosures of which are hereby incorporated by reference herein in their entirety and made part of the present U.S. utility patent application for all purposes.

BACKGROUND OF THE INVENTION

The described invention relates in general to two and three dimensional biocompatible structures that further include scaffolds of micro-scale or nano-scale fibers or combinations thereof, and more specifically a system for manufacturing a synthetic organ, such as a trachea, manufactured from such fibers.

In mammalian anatomy, the trachea (or windpipe) is a tube that connects the pharynx or larynx to the lungs, thereby allowing the passage of air between these structures (see FIG. 1). The trachea is lined with pseudostratified ciliated columnar epithelium cells with goblet cells that produce mucus. This mucus lines the cells of the trachea to trap inhaled foreign particles that the cilia then direct upward toward the larynx and then the pharynx where it can be either swallowed into the stomach or expelled as phlegm. The trachea typically has an inner diameter of about 25.4 millimetres (1.00 in) and a length of about 10 to 16 centimeters (3.9 to 6.3 inches). It begins at the lower border of the larynx, level with the sixth cervical vertebra, and bifurcates into the primary bronchi at the vertebral level of thoracic vertebra T5, or up to two vertebrae lower or higher, depending on breathing.

Fifteen to twenty incomplete C-shaped cartilaginous rings reinforce the anterior and lateral sides of the trachea to protect and maintain the airway, leaving a membranous wall dorsally without cartilage. The trachealis muscle connects the ends of the incomplete rings and contracts during coughing, reducing the size of the lumen of the trachea to increase the air flow rate. The esophagus lies posteriorly to the trachea. The cartilaginous rings are incomplete to allow the trachea to collapse slightly so that food can pass down the esophagus. A flap-like epiglottis closes the opening to the larynx during swallowing to prevent swallowed matter from entering the trachea.

A number of diseases and conditions are known to affect the trachea including, for example, choking, tracheotomy (a surgical procedure on the neck to open a direct airway through an incision in the trachea), tracheomalacia (weakening of the tracheal cartilage), tracheal collapse (in certain animals such as dogs), tracheobronchial injury (perforation of the trachea or bronchi), and Mounier-Kuhn syndrome (which causes abnormal enlargement of the trachea). Partial or complete loss of the trachea due to cancer or other diseases can have a catastrophic, if not fatal, effect on an animal or human.

A number of in vivo prostheses for luminal structures such as the trachea are known in the art. Typically these prostheses are formed by donor structures from cadavers or are manmade structures. However, these existing structures are subject to failure due to anastomotic stenosis, luminal stenosis, infection, dislocation, and migration, among other causes. Therefore, there is an ongoing need for artificial or prosthetic versions of organs such as the trachea that will provide the patient, human or otherwise, with a functioning replacement for the lost, damaged, or diseased organ.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a synthetic organ suitable for transplantation into a biological organism is provided. This synthetic organ includes a three-dimensional polymer scaffold, wherein the shape and dimensions of the polymer scaffold are based on a native organ, wherein the polymer scaffold further includes at least one layer of polymer fibers that have been deposited by electrospinning, and wherein the orientation of the fibers in the scaffold relative to one another is generally parallel, random, or both; and wherein the polymer scaffold has been preseeded with at least one type of biological cell prior to implantation into a biological organism, and wherein the at least one type of biological cell is operative to facilitate integration of the polymer scaffold into the organism so that the polymer scaffold may function in a manner significantly similar to or the same as the native organ.

In accordance with another aspect of the present invention, a system for manufacturing an artificial organ suitable for transplantation into a biological organism is provided. This system includes a three-dimensional preform that is based on the actual three-dimensional structure of a native mammalian organ; and an electrospinning apparatus, wherein the electrospinning apparatus is operative to deposit at least one layer of polymer fibers on the preform to form a polymer scaffold, and wherein the orientation of the fibers in the scaffold relative to one another is generally parallel, random, or both.

In yet another aspect of this invention, a synthetic organ suitable for transplantation into a biological organism is provided. This synthetic organ includes a three-dimensional polymer scaffold, wherein the shape and dimensions of the polymer scaffold are based on human trachea, wherein the polymer scaffold further includes at least one layer of polymer fibers that have been deposited by electrospinning, and wherein the orientation of the fibers in the scaffold relative to one another is generally parallel, random, or both; wherein the polymer scaffold has been preseeded with at least one type of biological cell prior to implantation into a biological organism, and wherein the at least one type of biological cell is operative to facilitate integration of the polymer scaffold into the organism so that the polymer scaffold may function in a manner significantly similar to or the same as the human trachea; and wherein the at least one type of biological cell further includes autologous cells or allogeneic cells, and wherein the autologous cells or allogeneic cells further include cord blood cells, embryonic stem cells, induced pluripotent cells, mesenchymal cells, placental cells, bone marrow derived cells, hematopoietic cell, epithelial cells, endothelial cells, fibroblasts or chondrocytes.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

Figure 1:
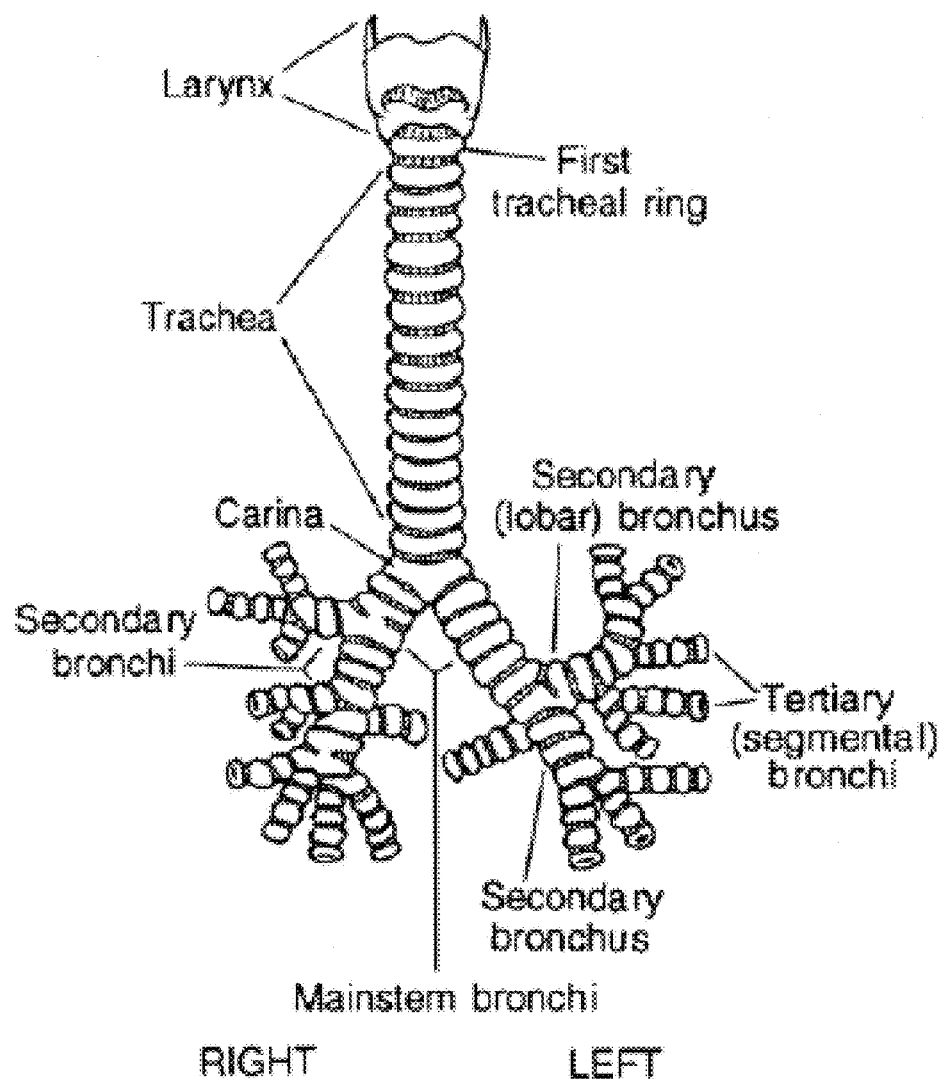
FIG. 1 is an illustration of the anatomy of a human trachea.
Figure 2:
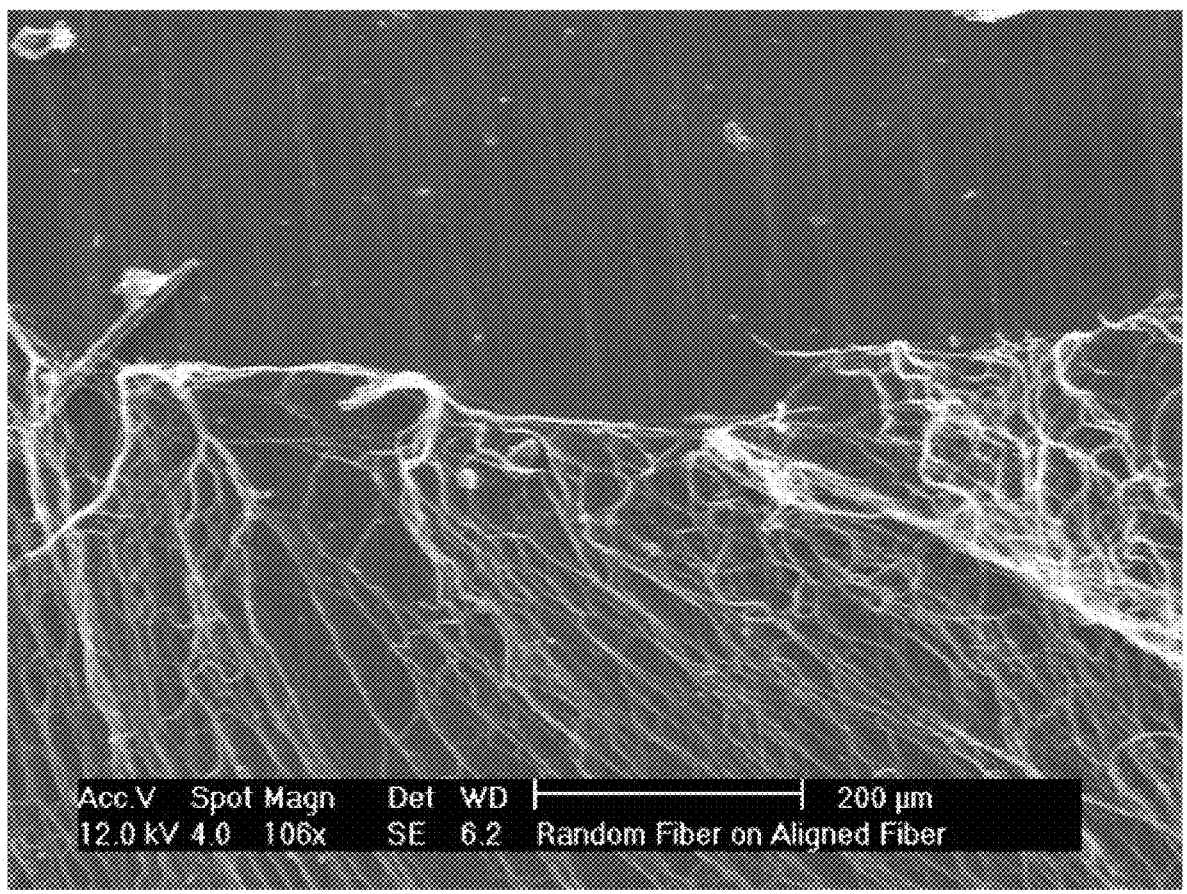
FIG. 2 is an SEM image of composite fiber scaffold that includes both oriented fibers and random fibers, manufactured in accordance with this invention.

The present invention relates generally to the development and construction of implantable artificial organs for humans and/or animals, and more specifically to an electrospinning process or method for manufacturing three-dimensional polymer microscale and nanoscale structures for use as scaffolds in the growth of biological structures such as hollow organs, luminal structures, or other structures within the body, particularly the trachea (see FIG. 1). However, the use of these scaffolds in creating or repairing other biological structures (e.g., esophagus, small intestine, large intestine, duodenum, jejunum, cardiovascular tissues, bone, etc,) is contemplated by and included in this invention In general, the broad utility of electrospun scaffolds for tissue engineering, wound healing, and organ replacement is clear (see, generally, *Modulation of Embryonic Mesenchymal Progenitor Cell Differentiation via Control Over Pure Mechanical Modulus in Electrospun Nanofibers*, Nama et al., Acta Biomaterialia 7, 1516-1524 (2011), which is incorporated by reference herein in its entirety, for all purposes). Exemplary versions of the manufacturing process of this invention include preparing a preform that is based on an actual native organ; electrospinning one or more layers of nanoscale (less than 1000 nanometers) or microscale (less than 50 microns) polymer fibers on the preform to form a nanofiber-based scaffold. The fibers are typically formed by electrospinning by extruding a polymer solution from a fiberization tip; creating an electronic field proximate to the fiberization tip; and positioning a ground or opposite polarity within the preform. The preform may be rotated to align the fibers on the preform or a second ground or polarity may be placed in the preform and rapidly switching the electric field to align the fibers. The microscale and nanoscale polymer fibers may be randomly aligned or maybe substantially parallel or both (see FIG. 2). These nanofiber structures may be seeded with one or more types of biological cells prior to implantation in the body to increase the rate of tissue growth into the scaffold. The polymer scaffold may include autologous or allogeneic cells such as cord blood cells, embryonic stem cells, induced pluripotent cells, mesenchymal cells, placental cells, bone marrow derived cells, hematopoietic cell, epithelial cells, endothelial cells, fibroblasts, chondrocytes or combinations thereof. These biological cells may be applied to the surface of the scaffold or distributed throughout the scaffold matrix utilizing perfusion within a bioreactor. With regard to the use of a bioreactor, Macchiarini et al., "Clinical Transplantation of a Tissue-Engineered Airway" (The Lancet 372:2023-2030 (Dec. 13, 2008) is incorporated by reference herein in its entirety for all purposes. Accordingly, an exemplary method for fabricating a trachea may include fabricating an electro-spun matrix, obtaining some group of patient cells, and combining the matrix and the cells in a bio-reactor thereby creating an artificial trachea. In some embodiments of this invention, the trachea is not pre-seeded, while in others the trachea is pre-seeded and then, optionally, cultured for a predetermined period of time in a bioreactor.

Choosing a material that accurately mimics the mechanical properties of the native trachea (or other organ) may promote proper stem cell differentiation and facilitate normal function of the replacement organ. Included materials may be non-resorbable for permanent implantation or may be designed to slowly degrade while the host body rebuilds the native tissue. In the latter case, the implanted prosthesis will eventually be completely resorbed. Permanent (i.e., non-resorbable) polymers may include polyurethane, polycarbonate, polyester terephthalate and degradable materials may include polycaprolactone, polylactic acid, polyglycolic acid, gelatin, collagen, or fibronectin. The fibers may be electrospun onto a preform with the desired prosthesis shape. An exemplary setup includes a 5 mm diameter rod with electrospun fiber being deposited onto the surface thereof. An exemplary mandrel (preform) is coated with Teflon or similar material to facilitate removal of the scaffold after deposition or a slight taper (e.g., about 1°) can be manufactured into the mandrel. Nearly any size or shape can be produced from the electrospun fibers by using a pre-shaped form and fiber deposition technique of this invention.

Figure 3:
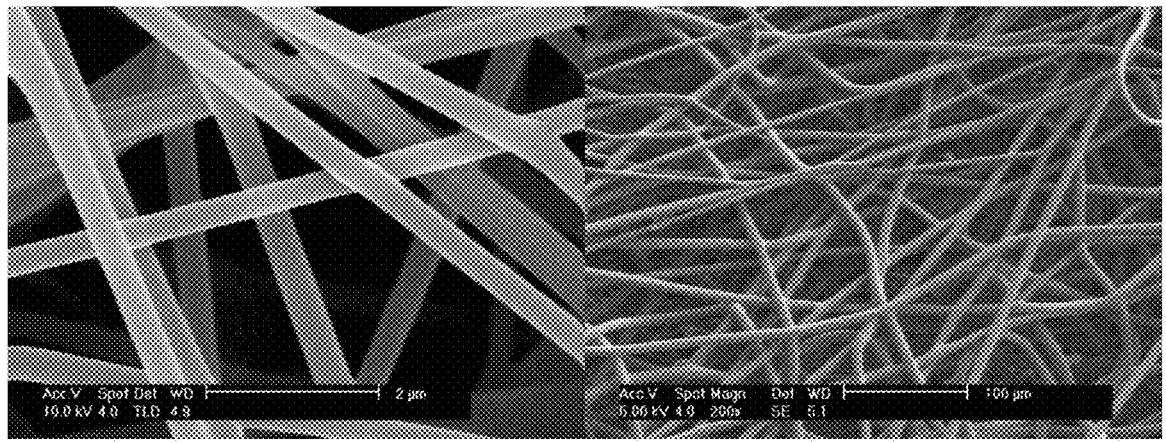
FIG. 3 provides an SEM image of a 200 nm diameter fiber (on the left) with pore sizes of a few microns and an SEM image of a 20 μm diameter fiber (on the right) with pore sizes of around 50 μm, both manufactured in accordance with this invention.
Figure 4:
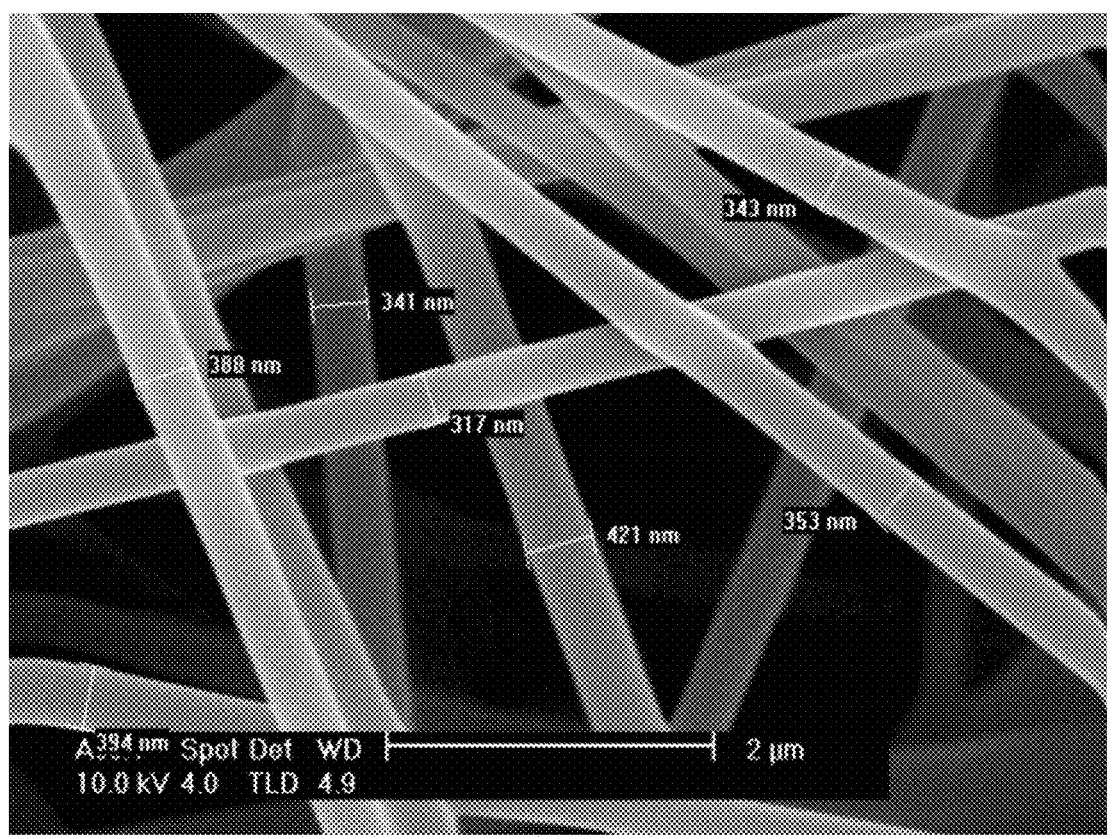
FIG. 4 provides another an SEM image of exemplary polymer nanofibers manufactured in accordance with this invention.

Closely mimicking the structural aspects of the native trachea (or other organ) is important with regard to replicating the function of the native trachea. By controlling the orientation of the fibers and assembling a composite structure of different materials and/or different fiber orientations it is possible to control and direct cell orientation and differentiation. Fiber orientation can be altered in each layer of a composite or sandwich scaffold in addition to the material and porosity to most closely mimic the native tissue. A properly constructed scaffold will permit substantially complete cellular penetration and uniform seeding for proper function and prevention of necrotic areas developing. If the fiber packing is too dense, cells may not be able to penetrate or migrate from the exposed surfaces into the inner portions of the scaffold. However, if the fiber packing is not close enough, then attached cells may not be able to properly fill the voids, communicate and signal each other and a complete tissue or organ may not be developed. Controlling fiber diameter can be used to change scaffold porosity as the porosity scales with fiber diameter (see FIGS. 3-4). Alternatively, blends of different polymers may be electrospun together and one polymer preferentially dissolved to increase scaffold porosity. Particles such as salt or sucrose may be included in the electrospinning process and deposited throughout the scaffold. These particles may later be dissolved for increasing scaffold porosity. The properties of the fibers can be controlled to optimize the fiber diameter, the fiber spacing or porosity, the morphology of each fiber such as the porosity of the fibers or the aspect ratio, varying the shape from round to ribbon-like. The precursor solution described below may be controlled to optimize the modulus or other mechanical properties of each fiber, the fiber composition, and/or the degradation rate (from rapidly biosoluable to biopersistent). The fibers may also be formed as drug eluting fibers, anti-bacterial fibers or the fibers may be conductive fibers, radio opaque fibers to aid in positioning or locating the fibers in an x-ray, CT or other scan.

The effects of mechanical strain on electrospun polymer scaffolds has been described in the literature (see, *Microstructure-Property Relationships in a Tissue Engineering Scaffold*, Johnson et al., Journal of Applied Polymer Science, Vol. 104, 2919-2927 (2007) and *Quantitative Analysis of Complex Glioma Cell Migration on Electrospun Polycaprolcatone Using Time-Lapse Microscopy*, Johnson et al., Tissue Engineering; Part C, Volume 15, Number 4, 531-540 (2009), which are incorporated by reference herein, in their entirety, for all purposes). Strains as low as 10% appear to rearrange and align the fibers in the direction of loading. This alignment increases with the applied strain until over 60% of the fibers are aligned within ±10% of the direction of applied stress. If cells are present during fiber rearrangement in vivo or in vitro, they could conceivably be affected by these changes depending on the overall rate of strain. Fiber alignment is retained following a single cycle of extension and release. This has significant biological implications for a broad array of future tissue-engineering operations. As cells move across such a substrate, biased motion is likely as locomotion is based on forming and then dissolving a series of focal adhesions. Formation of these adhesions along the fiber direction may be easier than for fibers perpendicular to that direction although this will be partially controlled by the spacing between the fibers. This has longer-term consequences for the eventual control of the architecture of tissues that develop upon such substrates.

Cellular mobility parallel to the fiber direction means that one could conceivably control and direct cell proliferation and migration by prestraining scaffolds to align the fibers in certain directions. This could result in tailored structures with highly aligned fibers and, as a result, highly aligned cells. Of additional importance is the fact that many envisioned applications of tissue-engineering scaffolds will involve the use of cyclic stresses designed to achieve specific architectures in the biological component of the developing tissue. These stresses or mechanical stimulations may also be used to help direct the cellular differentiation process (see, for example, *Compressive Forces Induce Osteogenic Gene Expression in Calvarial Osteoblasts*, Rath et al., Journal of Biomechanics 41, 1095-1103 (2008), which is incorporated by reference herein, in its entirety, for all purposes). If the scaffold experiences continuing hysteresis in which orientation increases versus the number of cycles the efficiency of the overall process will be greatly enhanced. For blood vessels, as an example, the application of cyclic pressures will produce preferential stresses that could cause significant alignment of the fibers in the circumferential direction. This could cause cellular alignment in the circumferential direction, potentially creating a more biomimetic arrangement.

In accordance with this invention, the process of electrospinning is driven by the application of a high voltage, typically between 0 and 30 kV, to a droplet of a polymer solution or melt at a flow rate between 0 and 50 ml/h to create a condition of charge separation between two electrodes and within the polymer solution to produce a polymer jet. A typical polymer solution would consist of a polymer such as polycaprolactone, polystyrene, or polyethersulfone and a solvent such as 1,1,1,3,3,3-Hexafluoro-2-propanol, N,N-Dimethylformamide, acetone, or tetrahydrofuran in a concentration range of 1-50 wt %. As the jet of polymer solution travels toward the electrode it is elongated into small diameter fibers typically in the range of 0.1-30 µm.

In preparing an exemplary scaffold for use as a tracheal prosthetic, a polymer nanofiber precursor solution is prepared by dissolving 2-30 wt % polyethylene terephthalate (PET) (Indorama Ventures) in a mixture of 1,1,1,3,3,3-hexafluoroisopropanol (HFIP) and trifluoroacetic acid and the solution is heated to 60° C. followed by continuous stirring to dissolve the PET. The solution may be cooled to room temperature and the solution placed in a syringe (e.g., 60 cc) with a blunt tip needle (e.g., 20 gauge). The nanofibers are formed by electrospinning using a high voltage DC power supply (Glassman High Voltage, Inc., High Bridge, N.J.) set to 1 kV-40 kV (e.g., +15 kV) positive or negative polarity, a 5-30 cm (e.g., 15 cm) tip-to-substrate distance, and a 1 µl/hr to 100 ml/hr (e.g., 10 ml/hr) flow rate. It is possible to use a needle array including a large number of needles (e.g., >1000) to increase system output. Approximately 0.2-3 mm (e.g., 1 mm) thickness of randomly oriented and/or highly-aligned fibers may be deposited onto the form, and polymer rings added, followed by an additional approximately 0.2-3.0 mm (e.g., 2 mm) of fiber added while the form is rotated. The scaffold may placed in a vacuum overnight to ensure removal of residual solvent (typically less than 10 ppm) and treated using a radio frequency gas plasma for 1 minute to make the fibers more hydrophilic and promote cell attachment. Samples may be storied in recloseable polyethylene bags, or the like.

In accordance with this invention, an exemplary preparation of electrospinning solution typically includes of polyethylene terephthalate (PET), polycaprolactone (PCL), polylactic acid (PLA), polyglycolic acid (PGA), polyetherketoneketone (PEKK), polyurethane (PU), polycarbonate (PC), polyamide (Nylon), natural polymers such as fibronectin, collagen, gelatin, hyaluronic acid or combinations thereof that are mixed with a solvent and dissolved. Suitable solvents include acetone, dimethylformamide, trifluoroacetic acid, hexa-fluoroisopropanol, acetic acid, dimethylacetamide, chloroform, dichloromethane, water, ionic compounds, or combinations thereof. A form is prepared for the deposition of nanofibers. Optionally, simulated cartilage or other supportive tissue may be applied to the form and the fibers are then sprayed onto or transferred onto a form to build up the scaffold. While the present invention may be useful for the preparation of a number of bodily tissues, including hollow organs, three-dimensional structures within the body such as trachea, esophagus, intestine or luminal structures, such as nerves (epineurium or perineurium), veins and arteries (aorta, tunica externa, external elastic lamina, tunica medica, internal elastic lamina, tunica inima) the preparation of a human trachea is shown by example herein. Other preforms for species such as primates, cats, dogs, horses and cattle may be produced.

Exemplary embodiments and variants of the present invention include the following general features and/or aspects: (i) a composite scaffold seeded with stem cells and promoted to differentiate into stratified tissue; (ii) separate scaffold layers or sheets seeded independently to form different types of tissue and then assembled together using sutures, adhesive or welding to form a tubular shape and the stratified tissue; (iii) a scaffold implanted without cells for immediate replacement of damaged tissue and allow for cellular migration in vivo; (iv) an electrospun fiber scaffold made from non-resorbable materials such as polyethylene terephthalate, polyurethane, polycarbonate, poly ether ketone ketone; (v) an electrospun fiber scaffold made from resorbable materials such as polycaprolactone, polylactic acid, polyglycolic acid; (vi) an electrospun fiber scaffold made from natural polymers such as collagen, gelatin, fibronectin, hyaluronic acid or any combination of material types; (vii) an electrospun fiber scaffold made from a single layer of oriented fibers or a composite comprising layers of oriented fiber to correspond to the native structure and help orient and differentiate cells (fiber orientation can be from a rotating mandrel (circumferential fiber alignment), a translating mandrel (longitudinal fiber alignment), or split ground method of using electrostatics to align the fiber); (viii) using a pre-shaped mandrel or form to deposit fibers onto to achieve a near net shaped organs; and (ix) using a pre-shaped mandrel or form to deposit fibers onto to achieve a near net shaped segment/patch. Various compounds may be embedded in the fibers of the scaffold using sub-critical or super-critical $CO_2$ for promoting cell growth, reducing inflammation, preventing infection, or combinations thereof.

With regard to fabricating/manufacturing a synthetic or artificial human trachea, in one or more embodiments of this invention, human tracheas were measured to determine the appropriate dimensions for synthetic trachea and bronchi. For example, with reference generally to FIG. 1, the upper elongated portion had a length of about 94 mm and a diameter of about 21 mm; the right bronchial portion had a length of about 30 mm and a diameter of about 16 mm; and the left bronchial portion had a length of about 30 mm and a diameter of about 14 mm. The two bronchial portions were set at an angle of about 54°, relative to one another. A preform for a human trachea was created from wood dowel rods, cut to length, and trimmed to match the diameter and cross-sectional shape determined by the human trachea measurements. The distal end of the trachea preform was beveled and the proximal ends of the right and left bronchus preforms were beveled to mate with the trachea preform. A metal pin was used to connect the right and left bronchus preforms to the distal end of the trachea preform. The form was then covered with non-stick aluminum foil wrapped around the entire construct to facilitate a uniform coating of nanofibers. Alternatively, a stainless steel mandrel may be machined from a rod to match a patient's dimensions and substituted for a wood mandrel. In accordance with this method, subsequent manufacturing steps include: (i) electro spinning at least one layer of nanoscale (i.e., <1000 nanometers) or microscale (i.e., >50 microns) polymer fibers onto the preform; and, optionally, (ii) applying at least one type of donor cells to the scaffold. Preferably, the fibers are formed by electrospinning, which as previously discussed, involves extruding a polymer solution from a fiberization tip; creating an electronic field proximate to the fiberization tip; and positioning a ground or opposite polarity within the preform. The preform may be rotated to align the fibers on the preform or a second ground or polarity may be placed in the preform and rapidly switching the electric field to align the fibers. In order to speed the growth of human tissue into the fiber preform, the fibers may be aligned by rapidly spinning the preform so that alignment of the structure produced by standard electrospinning while the fibers are drawn into a substantially parallel ordering by the tension created by spinning the form. Another method of forming parallel fibers in the preform is the split ground technique, in which fiber deposition rapidly alternates between two separate grounding plates within the preform or by alternating the electric field.

Other embodiments of this invention confer specific advantages such as making the scaffold more biomimetic, stronger, more elastic, more reliable, and more reproducible. With regard to nanofiber composition, PET demonstrates excellent biocompatibility, but is a relatively stiff polymer compared to human tissue. To more closely mimic the natural elongation or stretchiness of a native trachea, varying concentrations of PU were blended with PET to form a core/shell structure. PET and PU were both dissolved separately in HFIP and then these separate solutions were combined immediately before electrospinning to achieve desired final concentrations. For example, 30 ml of 8 wt % PET+HFP was combined with 80 ml of 3 wt % PU+HFP to arrive at a 50% PET/PU blend.

Figure 5:
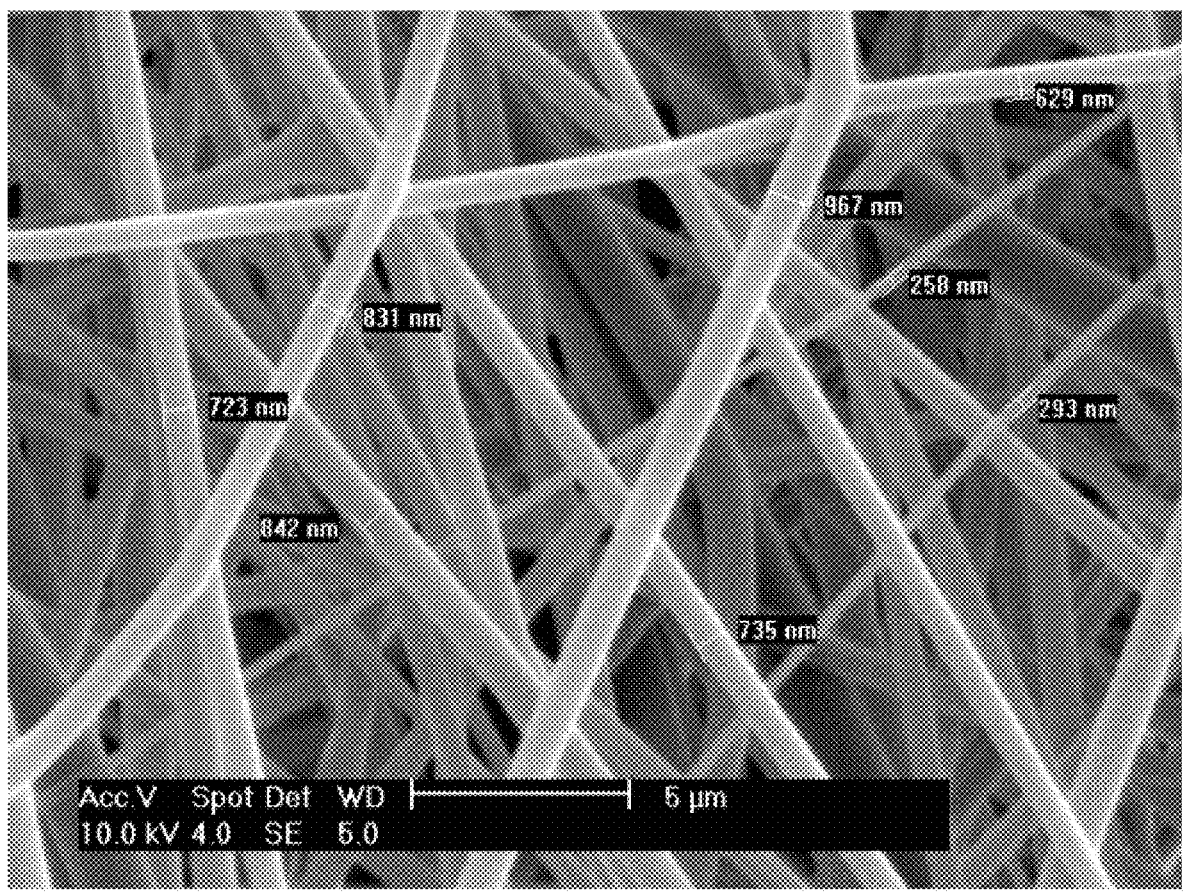
FIG. 5 is an SEM image of a blend of 50% polyethylene terephthalate and 50% polyurethane (PET/PU) depicting sub-micron diameter fibers, manufactured in accordance with this invention.

Examples 1-3, presented below, illustrate that a 50% PET/PU blend demonstrates increased strength and elongation and an increase in suture retention strength compared to a pure PET nanofiber scaffold. Also, when a trachea scaffold was made using pure PU (hardness of 80 A) it did not clearly demonstrate acceptable qualities; however, electrospinning using stiffer polyurethane compounds (e.g. hardness of 75 D) may provide an improved scaffold that includes only PU. FIG. 5 is an SEM image of 50% blend of PET/PU demonstrating sub-micron diameter fibers.

EXAMPLE 1

PET/PU

| 50% PET 50% PU Stress-Strain Data | | | |
|---|---|---|---|
| Sample | UTS | Elongation | Modulus |
| 1 | 4.61 | 284.35 | 20.27 |
| 2 | 4.41 | 319.75 | 17.98 |
| 3 | 4.33 | 257.27 | 17.50 |
| 4 | 4.43 | 254.15 | 21.30 |
| 5 | 4.78 | 230.2 | 19.99 |
| Average | 4.51 | 269.14 | 19.41 |
| Standard Deviation | 0.18 | 34.19 | 1.61 |

| 50% PET 50% PU Suture Retention Strength | | |
| --- | --- | --- |
| Sample | Force (N) | Force (lbs) |
| 1.5 mm 50% PETPU as-spun | 22.779 | 5.121 |
| 1.5 mm 50% PETPU as-spun | 22.414 | 5.039 |
| 1.5 mm 50% PETPU as-spun | 19.7785 | 4.4464 |
| 1.5 mm 50% PETPU as-spun | 18.375 | 4.1311 |
| 1.5 mm 50% PETPU as-spun | 29.327 | 6.593 |
| Average | 22.53 | 5.07 |
| Standard Deviation | 4.22 | 0.95 |

EXAMPLE 2

PET

| 100% PET Stress-Strain Data | | | |
| --- | --- | --- | --- |
| Sample | UTS | Elongation | Modulus |
| 1 | 1.55 | 70.87 | 11.72 |
| 2 | 2.09 | 229.15 | 22.4 |
| 3 | 2.48 | 172.92 | 24.25 |
| 4 | 2.05 | 93.78 | 27.9 |
| 5 | 1.9 | 127.1 | 12.56 |
| Average | 2.01 | 138.76 | 19.77 |
| Standard Deviation | 0.34 | 63.45 | 7.24 |

| 100% PET Suture Retention Strength | | |
| --- | --- | --- |
| Sample | Force (N) | Force (lbs) |
| 1.5 mm PET as-spun | 18.07579329 | 4.0636 |
| 1.5 mm PET as-spun | 14.0732835 | 3.1638 |
| 1.5 mm PET as-spun | 15.45934935 | 3.4754 |
| 1.5 mm PET as-spun | 12.39363502 | 2.7862 |
| 1.5 mm PET as-spun | 16.65503131 | 3.7442 |
| Average | 15.33 | 3.45 |
| Standard Deviation | 2.21 | 0.5 |

EXAMPLE 3

PU

| 100% PU Stress-Strain Data | | | |
| --- | --- | --- | --- |
| Sample | UTS | Elongation | Modulus |
| 1 | 6.04 | 264.56 | 1.08 |
| 2 | 4.49 | 212.49 | 0.78 |
| 3 | 6.37 | 288.48 | 1.05 |
| 4 | 5.79 | 295.8 | 0.85 |
| 5 | 8.13 | 344.74 | 1.16 |
| Average | 6.16 | 281.22 | 0.98 |
| Standard Deviation | 1.31 | 48.22 | 0.16 |

| 100% PU Suture Retention Strength | | |
| --- | --- | --- |
| Sample | Force (N) | Force (lbs) |
| PU 1.5 mm | 17.19 | 3.86 |
| PU 1.5 mm | 12.33 | 2.77 |
| PU 1.5 mm | 8.94 | 2.01 |
| PU 1.5 mm | 23.07 | 5.19 |
| PU 1.5 mm | 9.77 | 2.2 |
| Average | 14.26 | 3.21 |
| Standard Deviation | 5.88 | 1.32 |

Figure 6:
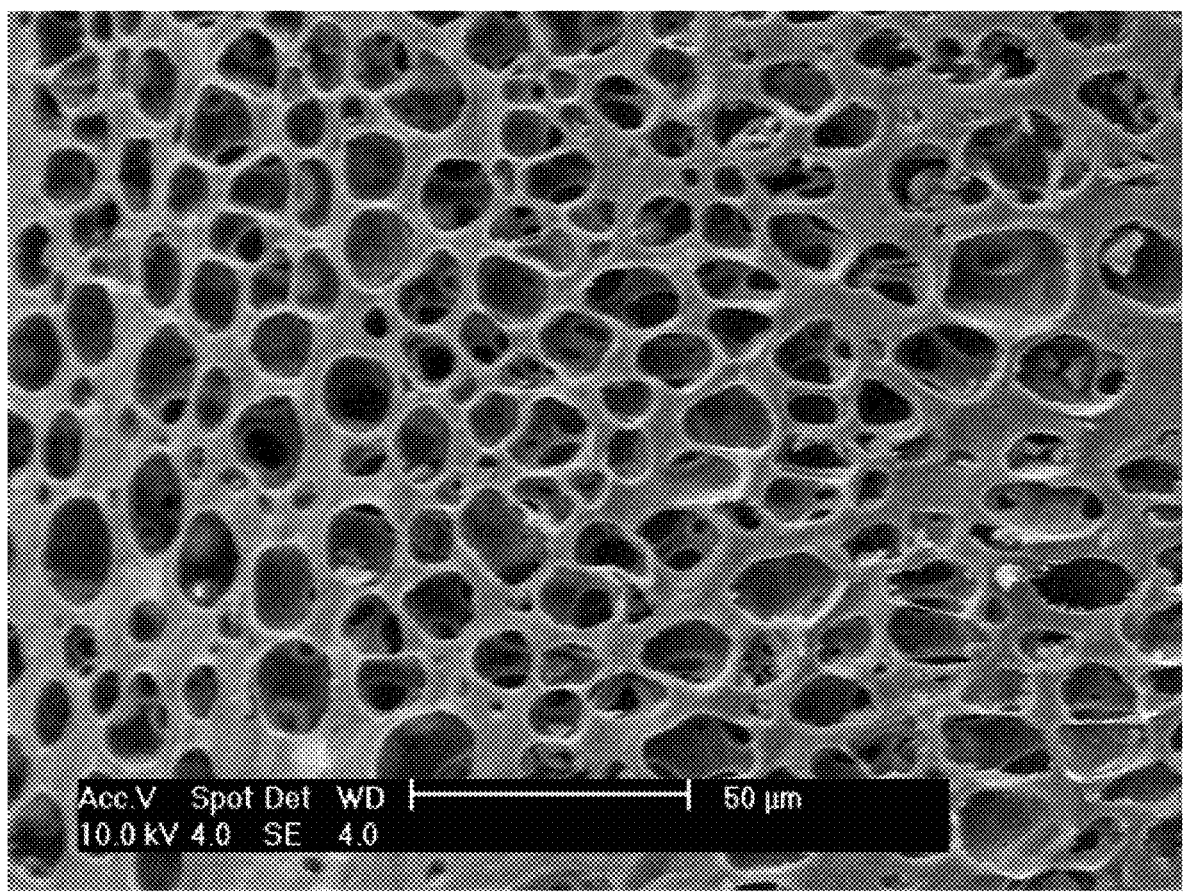
FIG. 6 is an SEM image of a cross-section through a cast, porous polyurethane (PU) sheet manufactured in accordance with this invention.

Regarding the composition of the cartilage rings included on the synthetic trachea of the present invention, other embodiments utilize solid PET rings that are custom injection molded to size or cut from a larger sheet to the desired size. These solid strips are then melted and wrapped around the fiber coated mandrel and held in place until sufficiently cool. While suitable for their purpose, these solid cartilage rings are typically very stiff, making it difficult for a needle to be passed therethrough for suturing and not consistently permitting desired levels of cellular in-growth. By dissolving 10 wt % of PU in a 50:50 volume mixture of tetrahydrofuran (THF) and dimethylformamide (DMF), a phase separation phenomenon is achieved during evaporation with 50% relative humidity (RH) or higher at room temperature. This phase separation creates 10-30 μm diameter pockets throughout the thickness of the polymer-only cast sheet as shown below in FIG. 6, which is an SEM image of the cross section through a cast porous PU-only sheet. It most cases, without adequate humidity, phase separation does not occur and pores are not formed in the cast sheet. Cartilage rings can be cut from sheets of this porous PU and glued to the nanofiber coated mandrel by using a 3 wt % PU+HFP solution. These porous rings are much more flexible, can easily be sutured, and allow cellular infiltration which presumably makes the synthetic trachea more biomimetic. The cartilage rings may be partially or wholly encased within the fiber scaffold and typically extend partially around the trachea's circumference. Drugs, growth factors, and other compounds may be injected into the rings for post-operative release. Some embodiments of this invention include straight, as opposed to bifurcated, tracheas that include the subglottic region of the esophagus. The subglottic region is the area located directly below the vocal cords and contains the cricoid cartilage. Synthetic tracheas manufactured in accordance with the present invention typically include one or more structures that mimic the cricoid cartilage.

Consistency and reproducibility are technical challenges often encountered in the manufacturing of artificial or synthetic organs. In one embodiment, the synthetic tracheas of the present invention are made using a single mandrel that rotates in place while up to four needles deposit fiber onto the mandrel. While effective, this manufacturing configuration may result in uneven fiber deposition and undesirable fiber pileups occurring across the length of the scaffold. One embodiment of this invention overcomes this problem and effectively doubles production capacity by joining two mandrels together and placing the mandrels into a stage that translates from side to side while still rotating the mandrels. This manufacturing configuration includes eight needles operating simultaneously (more are possible) and produces two scaffolds at a time, thereby demonstrating the scalability of this general approach to manufacturing the polymer fiber scaffolds and artificial organs of the present invention. Moving the mandrel (i.e., preform) side-to-side during deposition provides a more uniform fiber coating and prevents fiber pileups from occurring.

Most synthetic polymers are very hydrophobic and do not readily promote cell adhesion. Nearly all commercially available cell culture products are treated using an argon plasma or a corona treatment to make the surfaces thereof more hydrophilic (see, *Plasma Treatment of Textiles—Synthetic Polymer-Base Textiles*, Kang and Sarmadi, AATCC Review, Vol. 4, Issue 11, 29-33 (2004), which is incorporated by reference herein in its entirety for all purposes). For example, tissue culture polystyrene (TCPS) includes polystyrene that has been plasma treated for improved cell culture. A simple method for quantifying surface energy is to use a sessile water drop and measure the wetting angle. PET and PU, discussed above, are both very hydrophobic with water contact angles of about 131°, where 180° is perfect non-wetting and 0° is perfect wetting. However, a 1-minute plasma treatment produces perfect wetting with both materials (see TABLE 1, below) and significantly improves cell adhesion.

TABLE 1

Effect of Plasma Treatment on Wetting

| | Before Plasma Treatment | After Plasma Treatment |
|---|---|---|
| Polyethylene Terephthalate | | |
| Average Water Contact Angle | 131.0° | 0° |
| Polyurethane | | |
| Average Water Contact Angle | 130.8° | 0° |

In addition to increasing the surface energy of a polymer fiber scaffold by subjecting it to a plasma treatment, the surface thereof may also be functionalized, etched, or otherwise modified by attaching specific proteins, synthetic peptides, or other compounds to enhance cell growth, or promote/inhibit cell differentiation (see, for example, *A Defined Glycosaminoglycan-Binding Substratum for Human Pluripotent Stem Cells*, Klim et al., Nature Methods, Vol. 7, No. 23, 989-996 (2010), which is incorporated by reference herein in its entirety for all purposes.)

An exemplary method for manufacturing a human trachea in accordance with an exemplary embodiment of the present invention includes the steps of: (i) cleaning the preform and other parts involved; (ii) configuring the parts involved; (iii) initiating electrospinning to deposit polymer fibers on the preform to create a scaffold; (iv) assembling tracheal rings on the scaffold; (v) resuming electrospinning to deposit additional polymer fibers on the scaffold and tracheal rings; (vi) removing the scaffold from the preform mandrel; (vii) heating and plasma treating the scaffold; (viii) visually inspecting and verifying important dimensions of the scaffold; and (ix) packaging and shipping the product. A sterilization step may be included.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A method of manufacturing a synthetic organ, the method comprising:
    creating an electronic field of about 1-40 kV proximate to a fiberization tip;
    positioning a first ground within a preform having a three-dimensional shape mimicking a native mammalian organ within a patient population;
    positioning a plurality of porous synthetic cartilage rings on the preform, wherein the porous synthetic cartilage rings consist only of polyurethane, and wherein the porous synthetic cartilage rings are cut from a cast porous polyurethane sheet;
    rotating the preform;
    extruding from the fiberization tip a polymer solution comprising a polymer blend and a solvent, wherein the polymer blend comprises polyethylene terephthalate and polyurethane; and
    depositing by electrospinning at least one polymeric electrospun fiber on the preform.

2. The method of claim 1, wherein the native mammalian organ is a human trachea.

3. The method of claim 1, wherein the polymer blend further comprises a polymer selected from the group consisting of silicone, polycarbonate, polyether ketone, polycaprolactone, polylactic acid, polyglycolic acid, polyetherketoneketone, polyamide, collagen, gelatin, fibronectin, hyaluronic acid, and combinations thereof.

4. The method of claim 1, wherein the solvent is selected from the group consisting of acetone, dimethylformamide, trifluoroacetic acid, hexafluoroisopropanol, acetic acid, dimethylacetamide, chloroform, dichloromethane, water, ionic compounds, and combinations thereof.

5. The method of claim 1, wherein the polymer solution further comprises an additive selected from the group consisting of fluorescence compounds, radio opaque compounds, anti-bacterial compounds, growth hormones, conductive compounds, ceramic compounds, metallic compounds, oxygen sensing compounds, radioactive compounds, cell growth promoting compounds, proteins, hormones, cytokines, and combinations thereof.

6. The method of claim 1, further comprising positioning a second polarity within a preform.

7. The method of claim 1, further comprising preseeding the at least one polymeric electrospun fiber with at least one type of biological cell.

8. The method of claim 7, wherein the at least one type of biological cell is selected from the group consisting of autologous cells, allogeneic cells, cord blood cells, embryonic stem cells, induced pluripotent cells, mesenchymal cells, placental cells, bone marrow derived cells, hematopoietic cells, epithelial cells, endothelial cells, fibroblasts, and chondrocytes.

9. The method of claim 1, further comprising increasing a surface energy of the at least one polymeric electrospun fiber by using a radio frequency plasma treatment, using a corona treatment, or attaching a compound.

10. The method of claim 1, further comprising embedding a compound into the at least one polymeric electrospun fiber by sub-critical or super-critical $CO_2$.

11. The method of claim 1, wherein the native mammalian organ is a human trachea having at least one bronchus.

* * * * *